United States Patent [19] [11] Patent Number: 4,587,102
Nagatomo et al. [45] Date of Patent: May 6, 1986

[54] MULTI-LAYER ANALYSIS ELEMENT UTILIZING SPECIFIC BINDING REACTION

[75] Inventors: Shigeru Nagatomo; Yukio Yasuda; Nobuhito Masuda; Hajime Makiuchi; Masaki Okazaki, all of Kanagawa, Japan

[73] Assignee: Fuji Photo Film Co., Ltd., Kanagawa, Japan

[21] Appl. No.: 637,324

[22] Filed: Aug. 2, 1984

Related U.S. Application Data

[63] Continuation of Ser. No. 446,110, Dec. 2, 1982, abandoned, which is a continuation-in-part of Ser. No. 361,022, Mar. 23, 1982, abandoned, which is a continuation-in-part of Ser. No. 311,806, Oct. 15, 1981, abandoned.

[30] Foreign Application Priority Data

Jun. 5, 1981 [JP] Japan ................................. 56-86655

[51] Int. Cl.[4] ...................... G01N 21/78; G01N 33/53
[52] U.S. Cl. ..................................... 422/56; 435/805; 436/810
[58] Field of Search .............................. 422/56, 57, 58; 436/810; 435/7, 805

[56] References Cited

U.S. PATENT DOCUMENTS

| 3,368,872 | 2/1968 | Natelson | 422/66 |
| 3,992,158 | 11/1976 | Przybylowicz et al. | 422/58 X |
| 4,144,306 | 3/1979 | Figueras | 435/14 X |
| 4,166,093 | 8/1979 | Smith-Lewis | 422/56 |
| 4,258,001 | 3/1981 | Pierce et al. | 422/56 |
| 4,264,560 | 4/1981 | Natelson | 422/58 |
| 4,292,272 | 9/1981 | Kitajima et al. | 422/56 X |
| 4,363,874 | 12/1982 | Greenquist | 435/805 X |

Primary Examiner—Arnold Turk
Attorney, Agent, or Firm—Sughrue, Mion, Zinn, Macpeak & Seas

[57] ABSTRACT

A dry type multilayer analysis element for assaying a concentration of a specific component utilizing a competitive immunological reaction comprises a detection element comprising a detection layer which receives a labelled complex formed as a result of the competitive immunological reaction or an optically detectable change formed dependent upon an amount of the labelled complex of the specific component and having further provided thereon the detection layer a reaction layer comprising a fibrous porous medium containing fine particles therein. The multilayer analysis element absorbs an amount of a sample solution necessary for the competitive immunological reaction so that the multilayer analysis element has high sensitivity and high reproducibility.

12 Claims, 4 Drawing Figures

4,587,102

MULTI-LAYER ANALYSIS ELEMENT UTILIZING SPECIFIC BINDING REACTION

CROSS REFERENCE TO RELATED APPLICATION

This application is a continuation of application Ser. No. 446,110, filed Dec. 2, 1982, which is a continuation-in-part of U.S. Ser. No. 361,022, filed Mar. 23, 1982, which is a continuation-in-part of U.S. Ser. No. 311,806, filed Oct. 15, 1981, all abandoned.

BACKGROUND OF THE INVENTION

Field of the Invention

This invention relates to a method for measurement of concentration of a substance which plays an important biochemical role step or of various substances derived from the living body (hereafter "specific component") using a protein capable of specifically binding the substance through competitive reaction. This invention further relates to a multilayer analysis element comprising a reaction layer—where the aforesaid specific substance is reacted with a protein capable of specifically binding the same—and a detection element comprising a detection layer where a signal formed by undergoing a change in proportion to concentration of a substance of analytical interest is received. The term "signal" is meant to refer to a detectable change that is directly or indirectly indicative of the presence and/or concentration of a substance to be determined (hereafter often referred to as "analyte"), a reaction or decomposition product of the analyte.

DEVELOPMENT OF THE INVENTION

In clinical examination, various methods where several reagent solutions are added to a testing liquid and the concentration of a specific component in the testing liquid is measured are known. In these methods, reaction reagents must be accurately weighed and thoroughly mixed in order to improve the reproducibility of the measurement results and, in some occasions, precipitates must be separated from supernatants by centrifugal techniques, which requires high skill.

To replace such conventional methods, apparatus which provides high reproducibility without requiring high skill by automating all such procedures have been developed. Such automated apparatus are convenient for measuring large amounts of tested liquids, but they have the serious disadvantage of high expense. In order to obviate the disadvantages of such automated apparatus, multilayer analysis elements in which reaction reagents are incorporated have been proposed as a simple analysis means where supply of reagent solutions is not substantially required so that high skill is not required. Such multilayer analysis elements are advantageous in that they are inexpensive as compared to the automated apparatus described above. While various proposals have been made with respect to multilayer analysis elements utilizing chemical reactions or enzymatic reactions, it is still difficult to measure trace components or components having structural specificity to a high degree.

In a method for the analysis of such components using reagent solutions, for example, it is known to utilize an immunological reaction. However, only a few recent proposals have been made with respect to such multilayer analysis films in which reagents for immunological reaction are incorporated. When one attempts to apply immunological reaction techniques to conventional multilayer analysis films, it is difficult to obtain satisfactory analysis data due to problems inherent to immunological analysis as will be later discussed.

In Japanese Patent Publication No. 21677/78 (the term "publication" means an examined patent application published for purpose of opposition, which is open to public inspection; hereafter the same), a multilayer analysis element comprising a spreading layer of a non-fibrous porous material and a reagent layer in which a medium such as gelatin or PVA is impregnated with a reagent. However, the volume of testing liquid that can be absorbed in a short period of time is merely several (2 or 3) $\mu l$ to 20 $\mu l$ per 1 $cm^2$ in the case of using isotropically porous materials such as "blushed" polymers (cellulose acetate polymers, etc., prepared in a manner as described in U.S. Pat. No. 3,992,158 issued to Przybylowicz et al which are isotropically porous, i.e., possesses porosity in all directions) normally available or colloidal materials such as gelatin, and such materials absorb 25 $\mu l$ of a testing liquid necessary for immunological analysis in a short period of time only with difficulty. Accordingly, detection sensitivity is poor.

In addition, a multilayer analysis element formed by laminating, in order, a spreading layer of a non-fibrous porous material, a reagent layer containing a mutually reactive substance which gives diffusible chemical species which can be detected, a light shielding layer, a detection layer and a transparent support has also been suggested (Japanese Patent Application OPI No. 40191/76; the term "OPI" indicates an unexamined published patent application open to public inspection). However, non-fibrous porous materials employed for such an analysis element do not ensure sufficient water retainment in a short period of time; thus, this analysis element also involves the disadvantage that only analytical data of poor sensitivity are obtained.

Further, in Japanese Patent Application OPI No. 24576/81, a multilayer analysis element comprising a transparent support, a reagent layer obtained by incorporating reagents into colloidal substances and a fibrous porous carrier layer for eliminating interfering substances in a testing sample is disclosed. However, incorporation of reagents (proteins capable of effecting specific binding) seriously inhibits the binding reaction with components effective for measurement so that poor detection sensitivity or a reduction in accuracy results.

A multilayer analysis film that is intended to use for immunological reaction taking inherent properties of immunological analysis into account is also known, as stated above.

For example, the invention described in Japanese Patent Application OPI No. 90859/80 (corresponding to U.S. Pat. No. 4,258,001 issued to Pierce et al) is characterized in that thermally stable organic polymer particles are adhered point-to-point using an adhesive comprising an organic polymer different from the aforesaid polymer particles and the thus formed three-dimensional particulate structure is used as the porous material layer described above. However, it is extremely difficult to prepare such a special material and such is also expensive. In addition, a disadvantage is that if the thickness of the particulate structure is increased to enable 25 $\mu l$ or more of a testing sample necessary for immunological analysis to be absorbed, the smoothness of the multilayer analysis element containing the particulate structure is seriously lowered so that upon spotting the measurement accuracy of optical density is decreased.

In Japanese Patent Application OPI No. 131089/78 (corresponding to U.S. Pat. No. 4,144,306), a multilayer analysis element comprising a reagent layer having incorporated therein an immunologically bound pair (antigen-bound antibody) and a layer for receiving diffused species provided thereunder is disclosed. In using this element, when a drop of test solution is spotted on the reagent layer, substitution-release type immunologically competitive reaction occurs between a known amount of an immunoligically bound pair (labelled antigen-bound antibody) previously present in the reagent layer and a specific component in the test solution and a released species which acquires diffusibility as a result of immunological reaction is diffused into the layer to receive the diffused species, where the released species is optically measured. However, in this method in which an unknown amount of antigen in a test solution is mutually reacted with the labelled antigen-bound antibody to thereby release the labelled antigen, such release occurs very slowly and, as a result, the detectable diffusible species is released in an extremely small amount; such results in markedly poor sensitivity and poor response. In particular, in the case of a component having molecular weight of several thousand (e.g., insulin, molecular weight ca. 5,600), only a calibration curve which is far from a standard calibration curve can be obtained even if incubation is conducted for 24 to 48 hrs. This technique is not suitable for rapid assay.

In general, a method in which an antigen in a test solution and a labelled antigen are competitively reacted with an antibody simultaneously at the same time with immunological reaction using liquid reagents or a method comprising primarily reacting an antigen and an antibody in a test solution provide far higher sensitivity. For effecting such methods, it is required that a reaction layer having therein either a labelled antigen or an antibody be separated from a reagent layer having therein an antibody or a labelled antibody be used instead of using a labelled antigen-bound antibody. In this case, reagents in the reagent layer are dissolved out with a test solution and substantially freely diffused into the reaction layer, where the reagents cause a competitive antigen-antibody reaction with an unknown amount of an antibody or antigen or antibody contained in the test solution.

The multilayer analysis element in accordance with this invention is a dry type analysis material suitable for quantitative analysis of a specific component utilizing the above described competitive antigen-antibody reaction.

As a result of extensive studies on analysis elements that maintain high sensitivity and reproducibility comparable to the prior art immunological assay method (which comprises weighing a test solution and mixing the same with reagents to cause reaction) and which enable simple operation without requiring high skill—characteristic of dry type analysis—the present inventors noted that in order to ensure high sensitivity and high reproducibility, it is necessary for at least 25 $\mu l$, desirably 50 to 200 $\mu l$, of a test solution to participate in a competitive immunological reaction, as in the prior art method of wet type in which a test solution is weighed and mixed with reagents to cause an immune reaction. The amount "at least 25 $\mu l$" is a considerably large amount as compared to the amount of analyte measured in conventional dry type multilayer analysis films which are mostly intended to utilize chemical reactions other than immune response and accordingly, these conventional analysis films cannot be employed for purpose of immunological examination as they are.

Based upon the foregoing, it has been found that a fibrous porous medium without a continuous coating is appropriate as an immunologically reactive medium which possesses a space capable of absorbing at least 25 $\mu l$ of sample solution.

Further, it has been found that this fibrous porous medium undergoes a change in shape, such as curling, due to absorption of a sample solution only with difficulty and such is extremely advantageous from the viewpoint of optical measurement.

SUMMARY OF THE INVENTION

An object of this invention is to provide a dry type multilayer analysis element of high detection sensitivity and high accuracy.

The multilayer analysis element of this invention is composed of:

a detection element comprising, if desired or necessary, a support transparent to optical measurement and a detection layer which receives a labelled complex formed as a result of competitive immunological reaction or an optically detectable signal depending upon the amount of the complex; and a reaction layer comprising a fibrous porous medium containing proteins capable of causing competitive immunological reaction which is provided on the detection layer.

Figure 1:
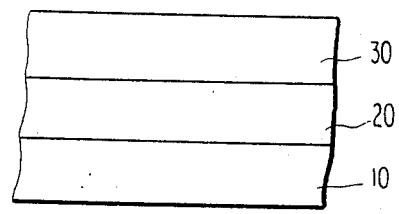
FIG. 1 is a cross sectional view representing a basic structure of the multilayer analysis element of this invention.
Figure 2:
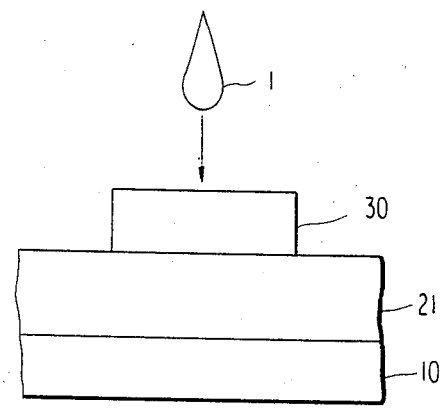
FIGS. 2 to 4 are cross sectional views representing various preferred embodiments of the multilayer analysis element of this invention.
Figure 3:
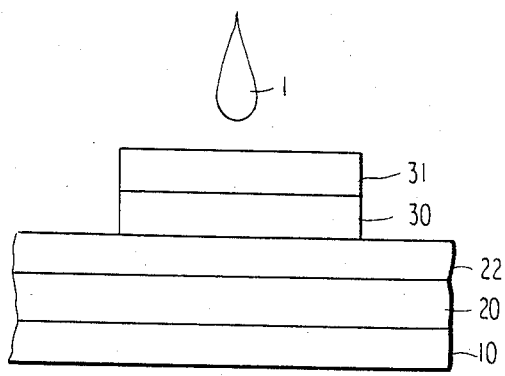
Figure 4:
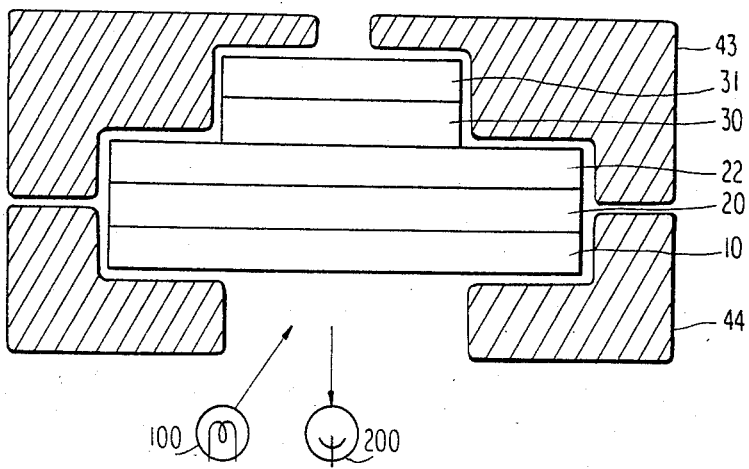

1: sample or testing solution
10: transparent support
20: detectio,n layer
21: detection layer having a light-shielding function
22: light-shielding layer
30: reaction layer
31: reagent layer
43, 44: frame
100: light source
200: photomultiplier.

PREFERRED EMBODIMENTS OF THE INVENTION

The optically detectable signal is generally a labelled complex formed as a result of a competitive immunological reaction in the presence of (1) a predetermined amount of a protein—which specifically recognizes and binds to a specific component (analyte) in a sample solution—and (2) a predetermined amount of a complex of the specific component and a label—which is also capable of reacting with the aforesaid specifically binding protein; alternatively, the optically detectable signal is a substance or species which is formed depending upon the amount of the labelled complex. Such a signal is a detectable change as has been defined hereinbefore.

The reaction layer functions, when contacting the element of this invention with a liquid containing an analyte, to cause the analyte or a reaction product of the analyte to interact with a protein contained in the reaction layer—which specifically recognizes and binds to the analyte—to produce a detectable change within the element. Thus, the reaction layer should not substantially contain a specific component (analyte), its analogue or a complex with the label. The term "not substantially" is meant to refer to a negligible amount or an amount of a specific component that does not impede competitive immunological reaction contemplated in the reaction layer.

The multilayer analysis element of this invention absorbs a sufficient amount (at least 25 $\mu$l, desirably 50 to 200 $\mu$l) of sample solution necessary for immunologically competitive reaction so that it provides high sensitivity and high reproducibility. Further, the multilayer analysis element enables analysis without any particular skill in a simple manner in an extremely short period of time.

The multilayer analysis element of this invention can be any shape insofar as it is suitable for analysis, but a sheet-like or film-like shape is generally preferred. In this case, it is preferred that the interface between the detection element and the reaction layer be one of intimate contact so as to yield an uniform wet state at the interface when a sample solution is spotted thereon and to have a minimized space from a contiguous layer to an extent that a liquid be smoothly transported to the contiguous layer therethrough.

The multilayer analysis element of this invention can be employed, for example, as described below.

Given a known amount of antibody (or antigen), the level of its corresponding antigen (or antibody) can be determined. It is preferred that an analyte (antigen or antibody) to be analyzed or quantitatively measured—which is contained in a sample solution—be labelled with a labelling substance and a given amount of the labelled substance be incorporated into a reagent layer provided separately from the reaction layer; a sample solution is then dropped thereon. Alternatively, a mixture obtained by previously mixing the labelled substance with a sample solution can also be dropped onto the multilayer analysis element. Such a reagent layer can generally be provided between the reaction layer and the detection layer, but it is preferred that it be located opposite the detection layer to the reaction layer as will be later discussed in more detail.

The analyte (antigen or antibody) in a sample solution and the labelled antigen or antibody, competitively react with a protein (corresponding antibody or antigen)—which specifically recognizes and binds to the antigen or antibody—in the reaction layer to form an immunological complex (usually at 0° to 65° C., preferablly 10° to 45° C. for 1 min. to 24 hrs. under normal pressure while conditions vary depending upon kind of analyte, mode of reaction and layer structure). Excess or unreacted analyte is permitted to separate from the complex and then diffused into the detection layer. The unreacted analyte (specific component) or the unreacted labelled antigen (or antibody) is optically measured as it is; or, an optically detectable signal is formed by reacting a reagent in proportion to the labelling substance and then optically measured. On the other hand, based upon the amount of labelled antigen (or antibody) obtained corresponding to a known amount of specific component or signal substance produced therefrom, a calibration curve can be previously prepared. By comparison to this calibration curve, the analyte (specific component) is measured or quantitatively determined.

In this invention, a specific component is primarily detected by optical means. Therefore, it is desired that a light-shielding layer be provided to eliminate the possibility that interfering substances other than a specific component to be measured (e.g., erythrocytes or hemoglobin in the case of using whole blood as a sample solution, or a fluorescence-labelled or dye-labelled antigen or antibody, etc.) participate in the optical measurement. In general, the light-shielding layer is inserted between the reaction layer and the detection layer; however, in the case where a light-shielding function is imparted to the reaction layer, the light-shielding layer can be omitted.

The reaction layer is composed of a fibrous porous medium having voids of about 20 to about 90%, preferably 50 to 90%.

Typical examples of fibrous porous media which can be employed in the reaction layer include natural fibers such as pulp, cotton, silk, wool, etc.; semisynthetic fibers such as cellulose esters, viscose rayon, etc.; synthetic fibers such as polyamides, polyesters, polyolefins, etc.; further, fibrous inorganic materials, e.g., glass fibers, colored glass fibers, asbestos, etc.—in the form of a textile (fabric that is woven or knitted), felt (fabric of matted, compressed animal fibers by applying heat, moisture or pressure), non-woven fabric (fibers more closely joined each other by chemical treatment or heating of fiber per se or fibers adhered to each other using an adhesive), etc.—or water-permeable paper, and the like can be used.

In more detail, there can be used a wide variety of fabrics such as natural fibers derived from plants, animals and minerals, etc.; and artificial fibers such as inorganic, regenerated, semi-synthetic and synthetic fibers, etc. Of various useful fabric forms, a plain weave which is formed by weaving warp and weft yarns alternately is preferably used. As for the warp and weft which compose such a plain weave, a desirable count ranges from 20 to 120. Of plain-woven fabrics, cotton fabrics of the type termed close cloth, canequim, broadcloth and poplin are preferably employed. In addition to other natural fibers woven in the same manners as the above-described cotton fabrics (e.g., kapok, flax, hemp, ramie, silk and so on), fabrics obtained by weaving mixed yarns of chemical fibers as described above and fabrics obtained by weaving chemical fiber yarns in the same manner as in the above-described cotton fabrics can also be employed.

The fibers described above can be used in the reaction layer in the form of non-woven fabrics formed into a cloth shape, not in the textile form.

Paper which can be used in the reaction layer can be freely chosen so long as it is water permeable. More specifically, a filter paper giving voids of about 20 to about 90% can be used; particularly preferred is thin, fine filter paper. Indian paper or Japanese paper such as paper made of paper mulberry or Mitsumata, etc. can also be employed. Not only natural cellulose paper but also synthetic paper (made of, e.g., polystyrene, polyester, polyethylene, polypropylene, etc.) obtained by paper-making fibers of synthetic high molecular weight substances—which possesses water permeability—, asbestos, glass fiber filter paper, etc., can also be employed as the reaction layer.

Further, the incorporation of fine particles (having a particle size of about 1 $\mu$m to about 1 mm, preferably 10 to 300 μm) of dextran, agarose, acrylamides, cellulose, etc., into these fibrous porous materials by intertwining the particles with these materials increases water-retention capability of a sample solution, which is advantageous.

While in the case where fine particles are incorporated into the fibrous material, the water-retention capability of the reaction layer can be further improved as a whole due to the water-retention capability of the fine particles while maintaining the fibrous nature of the porous medium, the fibrous porous nature should be maintained in the reaction layer as a whole and, accordingly, the amount of fine particles which can be incorporated (preferably thoroughly mixed) can naturally be set forth. In general, the amount of fine particles is in the range of up to 90 wt % based on the total weight of the reaction layer.

To incorporate a protein capable of specifically binding a specific component into fibrous porous media or materials containing fine particles, one can incorporate fine particles into fibrous materials to which the protein described above has previously been bound, either chemically (in a manner as described in, e.g., P. Cuatrecasas, *J. Biol. Chem.*, 245, 3059–3065 (1970), R. Axen et al., *NATURE*, 214, 1302 (1967), P. Cuatrecasas et al., *Methods in Enzymology*, 31, 345 (1969), etc.) or physically (in a manner as described in, e.g., K. Kato et al., *J. Biochem.*, 82, 261 (1977), etc.); or one can impregnate fibrous porous materials containing fine particles with an aqueous solution containing the protein described above followed by freeze drying. The freeze drying can be conducted in a conventional manner, e.g., by evacuating a freeze dried material under reduced pressure of about $10^{-2}$ to about $10^{31\ 4}$ mmHg to sublimation. Details of freeze drying and its conditions, etc. are described in *Methods in Enzymology*, 22, 33 (1971), published by Academic Press, New York (1971).

Because of its exellent water-retention property, the fibrous porous material described above retains the required amount (at least 25 μl) of spotted sample solution for a time period sufficient for the immune reaction to proceed. To exhibit this water-retention or absorbing capability of the porous medium more effectively, it is preferred that the reaction layer comprising the porous medium have an area smaller than that of the detection element. The detection element used herein is meant to refer to essentially the detection layer for receiving an optically detectable signal released or formed in the element and in addition thereto, can include various optional functional layers as will be later described.

It is preferred that the reaction layer be superimposed on the detection layer so as not to extend to or project from the detection element, which should ensure an area enabling appropriate optical measurement as a final result. In such a multilayer analysis element, when a sample solution is spotted thereon, undesired swelling of the reaction layer in the horizontal direction is only slightly observed; rather the reaction layer can swell only so as to increase the thickness thereof.

Accordingly the multilayer analysis element can retain a sample solution in the reaction layer for a time period sufficient for the immunologically competitive reaction to proceed, which results in a greater change of the signal amount. In addition, curling (which is observed with conventional known multilayer analysis films) does not occur; such is particularly advantageous in optical measurement.

The reaction layer can contain various reagents necessary for the immunological reaction and reactions which enable detection, except for labelled antigen which is incorporated into the detection layer. Addition of the labelled antigen should be avoided since the measurement sensitivity of an analyte is seriously decreased. Further, the reaction layer can be composed of two or more layers; for example, a sample solution can be sequentially exposed to two separate antigen-antibody reactions by incorporating different compositions into each of the two layers so that a detectable change, if it is weak, can be intensified. In this case, an antibody to an interfering component in a sample solution is incorporated; after the interfering component is thereby eliminated, an antigen-antibody reaction in which the analyte is used as a second antigen or ahtibody can be effected in the lower immunological reaction layer.

The reaction layer is provided on the detection layer, directly or indirectly via various functional layers such as a timing layer for controlling a rate of a liquid to be transported from the reaction layer, a light reflection layer or light absoprtion layer, etc.

The reaction layer, which is designed to have an area smaller than that of the detection layer in one embodiment of this invention, is of significance in that the reaction layer is physically restricted from expanding in the horizontal direction. Accordingly, it is difficult to specify the area thereof with a specific numerical value; rather, the area is determined depending upon or taking into account the necessary amount of a sample solution to be spotted, the kind and concentration of specific component (also called an analyte), etc., and production cost.

It is necessary that the detection element have or exhibit planarity upon measurement in order to maintain sufficient accuracy of measurement; accordingly, it is generally necessary for the detection element to comprise supporting means such as a frame, for mechanically compressing the element at the edge portions. On the other hand, it is sufficient that the reaction layer have an area sufficient to cover openings for spotting liquid therethrough. If the reaction layer is extended to the supporting means provided at the edge portions of the detection layer, i.e., if the reaction layer has the same area as that of the detection layer, such would result in waste of expensive reagents.

A protein which specifically recognizes and binds to an analyte is incorporated into the reaction layer. Representative methods for incorporation of the protein include:

(1) a method which comprises impregnating a fibrous porous medium with an aqueous medium containing the protein and then freeze drying in a conventional manner;

(2) a method which comprises linking an amino group or a carboxyl group of immunoglobulin to a fibrous porous medium directly or indirectly through a linking component by a physical means (adsorption, etc.) or a chemical means (covalent bond, etc.);

(3) a method which comprises, in the case of adding fine particles, adding the fine particles after binding the protein to the fine porticles through covalent binding or adsorption or through a linking component such as an Fc fragment complex, and so on.

The protein contained in the reaction layer exhibits a specific binding capability in an aqueous medium only when a predetermined volume of a sample solution is spotted thereon.

Accordingly, of the above methods, the method utilizing physical adsorption or the method which comprises impregnating a porous material with a protein-containing solution an then simply freeze drying the same—resulting in a state where the protein remains mixed—is preferred as compared to the method in which the protein is immobilized by, e.g., covalent linking, etc., since inactivation upon spotting a sample solution is minimized and binding capability is rapidly exhibited.

The protein capable of specifically binding a specific component (analyte) to be measured is determined depending upon the analyte.

The specific component (analyte) which can be measured using the multilayer analysis element of this invention refers to a component having antigenicity or an antibody present in a solution containing a biological component or body fluids such as blood, serum, spinal fluid, saliva, etc.

Representative examples of analytes are shown below.

[1] Polypeptides, proteins, polysaccharides, nucleic acids and complexes thereof:

Complexes are bacilla, viruses, cell membranes, genes, nuclei, etc. The molecular weight of these complexes is at least 5,000, ordinarily 10,000 or more. Polypeptides and proteins generally have a molecular weight of from 5,000 to 5,000,000, usually 20,000 to 1,000,000. In the case of peptide hormones, the molecular weight thereof generally ranges from 5,000 to 60,000.

(a) Proteins (1) simple proteins:

protamine, albumin, globulins ($\alpha$- $\beta$- particularly immunoglobulin, IgG, IgA, IgE, IgM, IgD), screloproteins (structural proteins such as collagen, elastin, actin, etc.);

(2) conjugated proteins:

mucoprotein, chromoprotein, lipoprotein, nucleoprotein, glycoprotein, phosphoprotein;

(3) other proteins including enzymes and complements:

(b) Peptide hormones insulin, glucagon, somatotropin, corticotropin, gonadotropin, gastrin, secretin, pituitary hormone, etc., precursors thereof and metabolites thereof;

(c) Microorganism-originated antigenic polysaccharides:

coccus (Streptococcus, Staphylococcus, etc.), bacillus (bacillus anthracis, bacillus subtilis, clostridium tetani etc.) actinomyces (Actinomyces, etc.), eumycetes (nocardia, aspergillus, candida, etc.), rickettsia (typhus, tutugamushi disease, Rocky Mountain spotted fever, Q-fever, etc.), viruses (herpes, adenoid vegitation, albo, hepatitis, etc.) spirochaeta (syphilis, leptospira, treponema, etc.) and other pathogenic bacteria;

[2] Antigenic low molecular weight substances:

Antigenic low molecular weight substances have a molecular weight of generally from 100 to 2,000, usually 125 to 1,000, e.g., drugs, agricultural chemicals, small peptides, amino acids, low molecular weight hormones and metabolites thereof.

(a) Drugs alkaloids (morphine, codeine, kinine, digoxine, etc.), 5- or 6-membered lactams (barbiturate, etc.), aminoalkyl benzenes (amphetamine, epinephrine, catecholamine, etc.), benzo-heterocyclic compounds (oxazepam, chlorpromazine, etc.), purines (theophylline, caffeine, etc.), vitamins (A, B complex, C, D, E, etc.), prostaglandins, antibiotics (penicillin, tetracycline, cephalosporin, etc.), aminoglycosides (gentamycine, kanamycine, etc.), other drugs (methadone, eprobamate, lidocaine, griseoflavin, etc.), and metabolites of these drugs.

(b) Agricultural chemicals halogenated biphenyls, phosphoric acid esters, thiophosphate, etc. and metabolites thereof.

(c) small peptides, amino acids, low molecular weight hormones, triiodothyronine, thyroxine($T_4$), encepharine, bradykinine, angiotensine I and II, and metabolites thereof.

Analysis of a component causing an immunological reaction using the multilayer analysis element of this invention is based upon the principle that a labelled specific component and an unlabelled specific component competitively react with a protein which specifically binds these specific components to thereby cause a change in signal and the amount of change of the thus changed signal is measured. As a method for labelling enabling one to measure a specific component based upon this principle, using a dye, etc., which makes optical measurement possible is excellent in simplicity and safety.

In the present invention, spectrophotometry, fluorophotometry, or the like can be utilized as the optical measurement system. In any case, optical measurement can be practiced by a reflection or transmission system, but a reflection system is preferred in that interfering substances can be eliminated thereby.

In spectrophotometry, ultraviolet rays, infrared rays, etc., can be utilized in addition to visible rays.

Fluorophotometry is effected with a fluorescent substance diffused into the detection layer, and the excitation light and fluorescence wavelength can be optionally chosen depending upon the purpose and utility desired.

Labelling of a specific component is carried out in a conventional manner as described in, e.g., Avrameas et al., *Immunochemistry*, vol. 8, pages 1175–1179 (1971) using glutaraldehyde cross linking technique; P. Nakane et al., *J. Histochem. Cytochem.*, vol. 22, pages 1084–1091 (1974) using periodic acid cross linking technique; T. Kitagawa et al., *J. Biochem.*, vol. 79, pages 233–236 (1976) using maleimide cross linking technique; D. Clyne et al., *J. Histochem. Cytochem.*, vol. 21, pages 233–240 (1973) using isocyanate cross linking technique; T. Ternynck et al., *Immunochemistry*, vol. 14, pages 767–774 (1977) using benzoquinone cross linking technique; U.S. Pat. No. 3,654,090 issued to A. H. W. M. Schuurs, B. F. Erlanger et al., *J. Biol. Chem.*, vol. 234, page 1090 (1959), *Methods in Enzymology*, vol. 22, page 33 (1971), published by Academic Press, New York, etc. Further, enzyme labelling can be effected by the methods described in the above citations; Eiji Ishikawa, Tadashi Kawai and Kiyoshi Miyai *Enzyme Immunoassay*, published by Igaku Shoin (1978); Wisdom, *Clin. Chem.*, vol. 22, page 1243 (1976); A. Voller et al., *The Enzyme Linked Immunosorbent Assay*, published by Flowing Publications, Guerney, Europe (1977); etc.

Fluorescein labelling is performed in a manner as described in SERIES OF CLINICAL TEST TECHNIQUE, vol. 4, subtitled "Immunoserological Test", edited by Tadashi Kawai, published by Igaku Shoin (1977), pages 97-102. When a dye or dye precursor is employed as a labelling substance, labelling is effected in a manner similar to using enzyme.

As enzymes for labelling, peroxidase, β-D-galactosidase, glucose-6-phosphate dehydrogenase or the like can be used. Fluorescein isothiocyanate (FITC), tetramethyl rhodamine isothiocyanate (TMRIT), etc. can be employed for fluorescence labelling.

Dyes for labelling are not overly limited, and any dyes can be employed so long as they are water-soluble and have relatively small molecular weight; useful dyes are described in HANDBOOK OF DYES; in more detail, merocyanine dyes as described in U.S. Pat. Nos. 2,493,748, 2,519,001 and 2,652,330, etc.; cyanine dyes as described in U.S. Pat. Nos. 2,238,213, 2,503,776, 2,537,880, 3,196,017 and 3,397,060; German Pat. No. 1,177,482, British Pat. No. 904,332, Japanese Patent Publications Nos. 14112/65 and 23467/65, etc.

Dye precursors can be used and are also not particularly limited, e.g., leuco dyes used in pressure sensitive recording materials, heat sensitive recording materials, etc., can be employed.

The detection layer receives a signal changed through competitive reaction (i.e., reaction products or detectable species released or formed in the element as a result of competitive reaction).

The detection layer is basically located below the reaction layer since it receives the detectable change that is produced in or released from the reaction layer. When an element includes a support, various functional layers such as a water-absorbing layer, etc. will usually, but not necessarily, be interposed in the element between the support and the detection layer. Further, functional layers such as a light reflection layer, a light absorption layer, etc. can be located over the detection layer. In the specification, the detection layer as an essential zone in the element and these functional layers are collectively termed the detection element.

The detection layer can be composed of the same fibrous porous media as is used for the reaction layer, e.g., textiles, non-woven fabrics, paper, etc.

Hydrophilic high molecular weight substances can be employed as binders for the detection layer.

Examples of binders which can be employed in this invention include natural hydrophilic high molecular weight substances such as gelatin, agarose, sodium alginate, carboxymethyl cellulose, methyl cellulose, etc.; hydrophilic synthetic high molecular weight substances such as polyacrylamide, polyvinyl alcohol, polyvinylpyrrolidone, sodium polyacrylate, polyhydroxyethyl methacrylate, copolymers containing acrylic acid (e.g., styrene-acrylic acid copolymer), copolymers containing maleic acid (e.g., maleic anhydridemethyl vinyl ether copolymer), etc.

In the case that a labelled specific component has a molecular weight of several hundred thousands as does IgG, agarose, polyacrylamide, sodium polyacrylate and copolymers containing acrylic acid are particularly preferred since macromolecular substances such as IgG can be appropriately retained in the network formed by these binder materials.

Incorporation of water-absorbing polymers into the detection layer is preferred since a signal can more effectively be collected in the detection whereby sensitivity as well as metering capability are improved. Further, when a water-absorbing polymer is incorporated is provided above, below or adjacent to the detection layer, a signal is more effectively collected and such is advantageous. As such water-absorbing polymers, hydrophilic synthetic or natural high molecular weight substances as described above can be employed singly or as a combination of two or more thereof. The use of gelatin in combination with polymers having a carboxy group, e.g., vinylpyrrolidone-acrylic acid copolymers makes swelling extremely easy and gives particularly preferred results.

In general, materials which provide capability of absorbing water of at least 5 times its dead weight, preferably at least 10 times, in 5 mins., are chosen for the water-absorbing layer.

Plural layers can be present between a support and a light shielding layer and these layers all function as the detection element as described above.

A reagent layer can be provided, if desired or necessary, above or below the reaction layer; however, taking the function of the reagent layer into account, it is preferred that the reagent layer be located usually over the reaction layer.

The reagent layer can contain a variety of reagents essential or desirable to effect immunological reaction and other reactions which render detection possible and render optical measurement of the formed signal possible, except for an antibody. For example, enzyme- or fluorescence-labelled antigens; enzyme substrates; co-enzymes such as NAD, NADH (NADP, NADPH, etc.); buffers for rendering pH constant; surface active agents, gelatin; stabilizers for bovine sermu albumin, etc.; coloring agents, etc. can be present. In addition, blocker or pretreatment reagents (e.g., thimerosal, salicylic acid, 8-anilino-1-naphthalenesulfonic acid (ANS), etc., for measurement of $T_4$) can also be present to render a testing component which is conjugated with a body component such as a protein or the like free.

A part of these reagents can also be incorporated into a spreading layer and/or a spreading-assisting layer, if desired or necessary, which can be provided above the reagent layer. Further, a part of these reagents (e.g., blocker reagents) can previously be mixed with a sample solution without incorporating the same into a multilayer analysis element, e.g., the reagent layer, and the resulting mixture can then be spotted onto the spreading layer or reagent layer.

It is often preferred that a timing layer be provided between the reaction layer and the detection element. The timing layer exhibits a function such that a sample solution can be retained in the reaction layer for a cetain period of time to thereby complete reaction and then makes the resulting reaction product diffuse the detection layer after a certain period of time. When this layer is provided, detection sensitivity and quantitative nature are further markedly improved. As materials for the timing layer, the aforesaid hydrophilic synthetic or natural polymers can be employed singly or in combination of two or more. Gelatin having various degrees of hardness is preferably used in the timing layer depending upon the purpose; in this case, strongly hardened gelatin can delay a rate of transporting a liquid and relatively mildly hardened gelatin can provide a mild degree of transportation of a liquid.

In addition to the above, various functional supporting layers or structural auxiliary layers (some of which have already mentioned hereinbefore) conventional in the art can be provided in the multilayer analysis element of this invention for purposes of supporting basic functions of the reaction layer and the detection layers or maintaining the structure thereof.

These supporting or auxiliary layers include, e.g., a spreading (or diffusing) layer to assist metering and spreading of a sample solution and a hematocyte separating layer (hematocyte interferes with optical measurement of a detectable change in a certain analysis and is separated using a material which retains macromolecular hematocyte therein) or an adhesive layer, all of which are optional. Details of these supporting or auxiliary layers are described in, e.g., U.S. Pat. No. 4,292,272.

The location of these auxiliary layers can easily be determined by one skilled in the art depending upon the functions thereof and it is believed to be unnecessary to provide detailed descriptions herein.

Layer thickness of essential and various optional functional layers included in the multilayer analysis element of this invention can vary depending upon kind of layer structure, functions required, etc., but the following layer thickness is generally desired:

reaction layer: 50 $\mu$m to 2 mm, preferably 200 $\mu$m to 1 mm
detection layer: 3 to 200 $\mu$m, preferably 5 to 50 $\mu$m
support: 50 $\mu$m to 2 mm, preferably 100 to 500 $\mu$m
reagent layer: 50 $\mu$m to 2 mm, preferably 100 to 500 $\mu$m
spreading layer: 50 to 500 $\mu$m
light-shielding layer: 1 to 50 $\mu$m, preferably 2 to 20 $\mu$m
water-absorbing layer: 3 to 200 $\mu$m, preferably 5 to 50 $\mu$m
timing layer: 2 to 50 $\mu$m.

When a fluorescent substance or a dye is employed as a label, it is optically detectable in the detection layer as it is and no particular reagents are required in the detection layer.

When a leuco dye, e.g., a leuco dye used for pressure sensitive recording paper or heat sensitive recording paper, is employed as a labelling substance, acidic substances such as acid clay are dispersed in a binder and the dispersion is coated on a support to yield the detection layer; a leuco dye-labelled specific component which is diffused or transported into the detection layer forms a color therein and optical measurement is possible.

In the case that an enzyme is employed as a labelling substance, the detection layer is formed by dispersing an enzyme substrate and a reducible dye precursor or a fluorescent precursor in a hydrophilic polymer and then coating the dispersion on a support. When labelling enzyme is, e.g., peroxidase, the detection layer can be formed (if desired or necessary in double layer form) by dispersing glucose, glucose oxidase (to generate hydrogen peroxide from glucose), 4-aminoantipyrine and 1,7-dihydroxynaphthalene (reduced dye precursor which is oxidized in the presence of hydrogen peroxide and peroxidase) in gelatin, agarose or polyacrylamide, etc., and coating the dispersion on a support. Further, in the case that the labelling enzyme is $\beta$-D-galactosidase, 4-methylumbelliferyl-$\beta$-D-galactopyranoside is dispersed in a hydrophilic polymer and a layer is formed on support from the dispersion.

In a preferred embodiment of this invention, a light shielding layer that permits effective passage of radiation used to detect an analytical change produced in the analysis element, is provided between the reaction layer and the detection layer, and it is preferred that the light shielding layer be a radiation absorbing layer or reflecting layer. The radiation absorbing layer is effective to absorb excitation wavelength to minimize a blank value due to reflection of the excitation wavelength, for example, when measurement of reflecting fluorescence is performed from the support side. It is possible to design a suitable system dependent on excitation wavelength and the emission wavelength. Various dyes, coloring agents, pigments, etc., can be employed in addition to yellow colloidal silver. On the other hand, a radiation reflecting layer is used in the case of measuring reflected spectral absorption from the support side and is obtained by dispersing a white powder, such as finely divided $TiO_2$, $BaSO_4$, etc., in a hydyrophilic high molecular weight binder in an amount of 1 to 25 wt % and forming a layer from the dispersion in a thickness as described above.

It is necessary that a labelled compound or a detectable reaction product which makes detection of a specific component possible be effectively collected in the detection layer. For this reason, materials having particularly excellent water-absorbing capability among the above described materials, e.g., hydrophilic natural or synthetic high molecular weight substances such as gelatin, polyvinyl alcohol, etc., are preferably employed for the detection layer. In addition, a filter paper, a glass fiber filter paper, a membrane filter, (or blushed polymer membrane), etc. can also be employed.

Further, in another preferred embodiment of this invention, substances having a strong interaction with a labelled compound or reaction product which makes detection possible, e.g., mordanting agents, are preferably incorporated in the detection layer in order to collect the compound or reaction product therein. As such mordanting agents, cationic polymers as described in Japanese Patent Application (OPI) No. 24694/80 (corresponding to U.S. Pat. No. 4,204,839); U.S. Pat. Nos. 2,484,430, 3,625,694, 3,758,445, 3,709,690, 3,488,706 and 3,557,006, e.g., a polymer of quaternary salts of 4-vinylpyridine and 2-methyl-1-vinylimidazole, poly-(N,N,N-trimethyl-N-vinylbenzyl ammonium chloride), etc.; other cationic polymers well known in the photographic art; and anionic polymers as described in Japanese Patent Application (OPI) No. 142562/82 can be used. Latexes of these polymers are preferred in view of improved diffusion resistance, ease in handling, etc.

To improve various efficiencies such as coating efficiency, diffusibility of diffusible compounds, reactivity, preservability, etc., various additives such as surface active agents, pH controlling agents, finely divided powders, antioxidants, other organic or inorganic additives can also be incorporated in the detection layer.

Supports used for the multilayer analysis element of this invention are transparent to optical measurement and it is preferred that the supports be water impermeable, depending upon necessity. Specific examples of light transmissible water impermeable supports include plastic films such as polyethylene terephthalate, cellulose esters (cellulose diacetate, cellulose triacetate, cellulose acetate propionate, etc.), polycarbonate of bisphenol A, polystyrene, polymethyl methacrylate, etc. and a glass plate. Known transparent supports having a thickness as described above can be used.

As supports for a multilayer analysis element in which a specific component is labelled with a fluorescent substance is employed, low fluorescence radiation transmitting supports such as polycarbonate of bisphenol A, cellulose esters polystyrene, etc. are particularly preferably employed.

In the case that a support is hydrophobic and provides poor adhesion to the hydrophilic binder in the detection layer, known auxiliary treatments such as treatment for rendering the surface of the support hydrophilic (e.g., ultraviolet irradiation, electron irradiation, a flame treatment, hydrolysis with an alkali, a plasma treatment, a glow discharge treatment, etc.), provision of a subbing layer comprising an appropriate adhesive for to the hydrophilic binders in both the support and the detection layer on the surface of the support, formation of minute uneven portions (brushing, electrolytic etching, etc.) at the surface of the support to a degree that light transmittance is not significantly decreased, etc. can be performed.

An aqueous sample solution-spreading layer often simply referred to as spreading layer) can be provided as the uppermost layer of the multilayer analysis element of this invention. The spreading layer has the effect of uniformly spreading a sample solution dropped onto the multilayer analysis element. In case that the reaction layer is composed of a woven fabric, nonwoven fabric or paper, the spreading layer can be omitted, of course.

For the spreading layer, fabrics which have been rendered hydrophilic are employed. As such fabrics rendered hydrophilic, there are fabrics that are cleaned and rinsed with water to defat the same followed by drying and fabrics that are, after cleaning and rinsing with water to defat the same, impregnated with a small amount of a surface active agent, a wetting agent, a hydrophilic polymer or a dispersion of finely divided powders of $TiO_2$ or $BaSO_4$ in a hydrophilic polymer. Techniques using fabrics which have been subjected to hydrophilic treatment as the spreading layer, kind of fabrics, layer thickness, etc., are described in detail in Japanese Patent Application OPI No. 164356/80, U.S. Pat. No. 4,292,272, etc. and can be applied to this invention in accordance with the description therein.

Hereafter this invention will be described in more detail with reference to the examples below.

EXAMPLE 1

(1) Hemisuccinamide of Thyroxine ($T_4$)

In 150 ml of dried tetrahydrofuran 1.65 g (0.002 mol) of thyroxine methyl ester hydrochloride was dissolved. To the resulting solution 300 $\mu$l (0.0021 mol) of triethyl amine and 200 mg. (0.0022 mol) of succinic anhydride were added. The mixture was stirred at 4° C. overnight to effect reaction.

After the reaction mixture was washed three times with a 10% saline solution, it was dried over anhydrous sodium sulfate followed by concentration under reduced pressure. The concentrate was subjected to column chromatography with a methanol-acetone (2:8) solvent using 30 g. of Sephadex LH-20. By checking the effluent by TLC, fraction of the product was obtained. The effluent was removed by distillation under reduced pressure and the residue was dissolved in methanol. To the resulting solution, water was added to crystallize. The crystals obtained were 1.48 g. and the yield was 82.5%.

(2) Binding of Thyroxine ($T_4$) Hemisuccinamide and Peroxidase

In 1 ml. of dioxane, 100 mg. (0.11 mmol) of thyroxine hemisuccinamide was dissolved. After cooling the resulting solution to $-15°$ C., 14 $\mu$l (0.11 mmol) of isobutyl chlorocarbonate and 15 $\mu$l (0.11 mmol) of triethyl amine were added thereto and the mixture vigorously shaken. A solution of 1.0 g. of peroxidase (POD) in 3 ml. of dioxane-water (1:1) cooled to 0° C. was added to the mixture. A 1N sodium hydroxide solution was added to the mixture. While maintaining pH of the mixture at 8.0 to 8.5, the mixture was stirred for 5 hrs. The reaction liquid was dialyzed overnight at 4° C. using a 0.02M sodium carbonate buffer (pH 8.5). Fractionation was performed using a Sephadex G-10 column (2×50 cm). For elution, a 0.05M phosphate buffer (pH 7.0) was used. After the effluent was fractionated by approximately 1.0 ml each, absorption at 280 nm and enzyme activity were measured and a fraction showing the maximum activity was chosen.

(3) Preparation of Multilayer Analysis Element for Thyroxine Measurement

Detection Element

By laminating or coating (i) to (iii) below in the order recited, a detection element was obtained and cut into 2 cm. squares.

(i) Support a colorless transparent cellulose triacetate film (thickness 130 $\mu$m)

(ii) Detection Layer 3.02 g. of gelatin, 18.0 g. of o-phenylenediamine and 20,000 U of glucose oxidase were coated per 1 $m^2$. Further, citrate-$NaH_2PO_4$ buffer (pH 4.8) was added to insure a buffering function. Layer thickness was 15 $\mu$m.

(iii) Light Shielding Layer 4.6 g. of gelatin and 36.2 g. of barium sulfate were coated per 1 $m^2$ onto the detection layer described above. Layer thickness was 12.6 $\mu$m.

(iv) Immunological Reaction Layer 0.9 g. of a cellulose filter paper (e.g., Toyo Filter Paper No. 5A made by Toyo Filter Paper Co., Ltd.) was well washed with purified water and dispersed in 20 ml. of purified water. To the dispersion 10N NaOH was added and the pH of the mixture adjusted to 12. While maintaining the pH at 11 to 12 with 10N NaOH, 40 ml. of a 5.0 wt % BrCN aqueous solution was dropwise added to obtain activated cellulose, during which the system was ice cooled below 20° C. After completing the reaction, the reaction mixture was filtered with a glass filter. After washing the residue with 1 liter of cold water, it was dispersed in 100 ml. of 0.1M $NaHCO_3$. To a 10-fold dilution of 1 ml. of antithyroxine rabbit sera (manufactured by CAPPEL Research Laboratories) with a 0.05M phosphate buffer saline (PBS) (pH 7.3), the aforesaid activated cellulose was added. After shaking overnight at 4° C., the mixture was filtered and the residue was dispersed in 0.15M NaCl. The dispersion was then filtered using a glass filter. To the residue, 100 ml. of 0.02M ethanolamine (the pH of which was adjusted at 8.0 using HCl) was added and the mixture was reacted at room temperature for 1 hr. Thereafter, the reaction product was washed with 1 liter of a 0.15M saline solution and then with 1 liter of a 0.05M phosphate buffer (pH 7.3) and dispersed again in 20 ml. of a 1% glucose solution. The dispersion was spreaded over and in fine nylon mesh, which was freeze dried as it was. The dry thickness after stripping of the nylon mesh was 0.9 mm. The material obtained was cut into 1 cm squares. The surface of the cut material was wet with water and then laminated on the detection element described above at the center thereof. The reaction layer thus obtained had voids of 80%.

(4) Measurement of Concentration of Thyroxine

The POD-labelled thyroxine (in an amount of 1 U calculated as POD activity) prepared in Example 1 (2) was mixed with 100 μl of a standard throxine solution (1 to 16 μg/dl). 100 μl of the mixture was dropped onto the multilayer analysis element prepared as described above, respectively, which was maintained at 37° C. Thirty mins. after dropping, reflection optical density (hereafter reflection density) was measured at 437 nm from the support side.

Results are shown in the table below were obtained.

TABLE 1

| Concentration of Tyroxine (μg/dl) | 1.0 | 2.0 | 4.0 | 8.0 | 16.0 |
|---|---|---|---|---|---|
| Reflection Density | 0.29 | 0.33 | 0.36 | 0.50 | 0.77 |

When the results were plotted on a graph, a linear relationship was seen between thyroxine concentration and reflection density. Accordingly, it is possible to quantitatively determine an unknown amount of thyroxine contained in a liquid sample by measuring reflection density.

EXAMPLE 2

(1) Preparation of Multilayer Analysis Element

A reagent layer as shown below was further provided on the immune reaction layer of a multilayer analysis element having the same structure as in Example 1 (3).

Reagent Layer

The same filter paper as was used in the reaction layer of Example 1 (iv) was cut into 1 cm. squares and impregnated with the POD-labelled thyroxine prepared in Example 1 (2) in an amount of 1 U/cm$^2$ (calculated as POD activity) followed by freeze drying ($10^{-3}$ mmHg in a freezer at $-20°$ C.). The thus obtained reagent layer was laminated onto the aforesaid immunological reaction layer.

(2) Measurement of Thyroxine Concentration

Onto the thus prepared multilayer analysis element, 100 μl of a standard thyroxine solution (1 to 16 μg/dl) was dropped. The element was maintained at 37° C. Thirty mins. after dropping, reflection density was measured at 437 nm from the support side. The following results were obtained.

TABLE 2

| Concentration of Thyroxine (μg/dl) | 1.0 | 2.0 | 4.0 | 8.0 | 16.0 |
|---|---|---|---|---|---|
| Reflection Density | 1.32 | 0.38 | 0.55 | 0.74 | 1.23 |

When the results were plotted, a linear relationship was seen between thyroxine concentration and reflection density. Accordingly, it is possible to quantitatively determine an unknown amount of thyroxine contained in a liquid sample by measuring reflection density.

EXAMPLE 3

(1) Fluorescein-Labelled Thyroxine (FITC-T$_4$)

(i) Synthesis of t-butoxycarbonylglycyl thyroxine methyl ester (Boc-Gly-T$_4$-OCH$_3$)

In 5 ml. of tetrahydrofuran (THF), 329 mg. (1.21 mmol) of t-butoxycarbonylglycine succinyl ester (Boc-Gly-OSu) was dissolved. On the other hand, 15 ml. of THF had dissolved therein 1.0 g. (1.21 mmol) of thyroxine methyl ester hydrochloride and a solution of 170 μl (1.21 mmol) of triethyl amine (Et$_3$N) in 3 ml. of THF was added to the resulting solution.

To the aforesaid Boc-Gly-OSu solution the thyroxine methyl ester solution was added while ice cooling. After permitting the same to warm to room temperature, the mixture was stirred for 1.5 hr. After letting the reaction mixture stand overnight, 25 ml. of distilled water and 50 ml. of ethyl acetate were added thereto and the mixture was extracted with ethyl acetate. The extraction was repeated three times using 25 ml. of ethyl acetate. The ethyl acetate layers were combined and dried over anhydrous magnesium sulfate. The liquid was concentrated using a rotary evaporator and subjected to gel chromatography using a column filled with Sephadex LH-20 (made by Pharmacia Co., Ltd.). As the solvent, a mixture obtained by mixing acetone and methanol in a proportion of 4:1 (volume) was used. While confirming by TLC, the objective fraction was taken and concentrated under reduced pressure followed by crystallization. The product was obtained in an amount of 950 mg. (yield 82.5%).

(ii) Removal of Boc 950 mg. (1 mmol) of Boc-Gly-T$_4$-OCH$_3$ synthesized in (i) above was dissolved in 10 ml. of trifluoroacetic acid and the solution was stirred for 10 mins. under ice cooling. The solvent was then removed by distillation at a temperature below 40° C. under reduced pressure. The residue was subjected to gel chromatography under the same conditions as in (i) to remove a fraction of the product. Crystallization of the fraction gave 700 mg. of the product (yield 82.5%).

(iii) Synthesis of Fluorescein isothiocyanic acid glycyl thyroxine methyl ester (FITC-Gly-T$_4$-OCH$_3$)

320 mg. (0.33 mmol) of Gly-T$_4$-OCH$_3$ trifluoroacetic acid salt obtained in (ii) and 47 μl. (0.33 mmol) of Et$_3$N were dissolved in 5 ml. of methanol. The resulting solution was added to a solution of 130 mg. (0.33 mmol) of FITC in 45 ml. of methanol. After reacting at room temperature for 24 hrs., the reaction mixture was distilled at temperature below 40° C. under reduced pressure. The residue was subjected to gel chromatography under the same conditions as in (i) to remove a fraction of the product. Crystallization was performed. Crystals obtained were orange and obtained in an amount of 290 mg. (yield 70%).

(2) Preparation of Multilayer Analysis Element for FITC-T$_4$ Measurement

Detection Element:

By coating or laminating (i) to (iv) below, a detection element was prepared and cut into 2 cm. squares.

(i) Support a colorless transparent cellulose triacetate film (thickness 130 μm).

(ii) Water Absorbing Layer

A 5% aqueous gelatin solution was mixed with a copolymer of vinyl pyrrolidone:acrylic acid=9:1 molar in a proportion of gelatin:copolymer=10:1 and the mixture was coated on the support. The gelatin amount after coating was 22.8 g/m$^2$ and the copolymer amount was 2.8 g/m$^2$ (dry basis for both). Layer thickness was 19 μm.

(iii) Detection Layer

A 5% gelatin aqueous solution and a copolymer of styrene and N,N,N-trimethyl-N-vinylbenzyl ammonium chloride (50:50) were coated as a layer in an amount of 3.02 g/m$^2$, respectively, dry basis, on the water absorbing layer. The layer thickness was 5 μm.

(iv) Filter Layer

To gelatin, 1% (based on the solid weight of gelatin) of 2-[2'-(α-sulfoctadecylamido)-ethylcarbamyl]-4-(2''-sulfo)phenylazo-1-naphthol as a dye and 1% (same basis as above) of 1-hydroxy-3,5-dichloro-2,4,6-triazine sodium salt as a hardening agent were added and the mixture was coated on the detection layer. Layer thickness was 5 μm.

(v) Immunological Reaction Layer

A glass fiber filter paper (Toyo Filter Paper GA-100, made by Toyo Filter Paper Co., Ltd.) having a thickness of 0.3 mm was cut into 1 cm. squares and impregnated with anti-T$_4$ serum (made by CAPPEL Research Laboratories) diluted with a 0.02M sodium phosphate buffer (pH 5.5) containing 0.5% bovine serum albumin followed by freeze drying ($10^{-3}$ mmHg in a freezer at $-20°$ C.). The freeze dried material was cut into 2 cm. squares and laminated on the detection element described above at the center thereof, the surface of which had been wet with water. The thus obtained reaction layer had voids of 70%.

(vi) Reagent Layer

The same glass fiber filter paper as used in the immune reaction layer was cut into 1 cm. squares and impregnated with an FITC-T$_4$ aqueous solution in an amount of 25 ng/cm$^2$ (calculated as FITC-T$_4$) followed by drying. The thus dried material was laminated onto the immune reaction layer described above.

The thus prepared multilayer analysis element was treated as in Example 1 (3) and then fluorescence was measured (excitation wavelength 490 nm; emission wavelength 520 nm). Quantitative results as shown below were obtained.

TABLE 3

| T$_4$ (μg/dl) | 1 | 2 | 4 | 8 | 14 | 20 |
|---|---|---|---|---|---|---|
| Relative Intensity of Fluorescence | 23 | 42 | 73 | 89 | 97 | 100 |

When these results were plotted on a graph, good correspondence was noted between thyroxine concentration and relative intensity of fluorescence. Accordingly, it is possible to quantitatively determine an unknown amount of thyroxine by measuring fluorescence intensity.

EXAMPLE 4

A multilayer analysis element was prepared as in Example 1 except that the immunological reaction layer was prepared by further incorporating antibody-immobilized particles therein as described below.

Immunological Reaction Layer

Immobilization of the antibody was performed as in Example 1 except that 1 g. of CN-Sepharose 4B (made by Pharmacia Co., Ltd.) was employed instead of cellulose filter paper activated with BrCN. Thus, anti-thyroxine antibody-immobilized Sepharose 4B was obtained. 1.0 g. of a filter paper (Toyo Filter Paper No. 5A made by Toyo Filter Paper Co., Ltd.) was wet with water to loosen its tissue and dispersed in water. The dispersion was well mixed with 1.0 g. of the antibody-immobilized Sepharose described above and the mixture was spread over and into a nylon mesh followed by freeze drying ($10^{-3}$ mmHg in a freezer at $-20°$ C.). The thickness thereof after stripping of the nylon mesh was 1.7 mm.

The concentration of thyroxine was measured as in Example 2 (2). Good correspondence was noted between thyroxine concentration and reflection density.

While the invention has been described in detail and with reference to specific embodiments thereof, it will be apparent from one skilled in the art that various changes and modifications can be made therein without departing from the spirit and scope thereof.

What is claimed is:

1. A multilayer analysis element for assaying a concentraion of a specific component in an aqueous medium utilizing a competitive reaction in the presence of a predetermined amount of a protein to be specifically bound to a specific component and a specific component labeled with a labeling substance which is capable of reacting with said protein to be specifically bound to said specific component, the multilayer analysis element comprising:

(A) a reaction element comprising a fibrous porous medium having a water-retention capability of at least 25 μl and fine particles of a high molecular weight material having a particle size of about 1 μm to about 1 mm which contains a protein to be specifically bound to a specific component to be assayed but does not substantially contain any specific component having binding capability to the protein, whereby when a sample solution is applied to said reaction element it is absorbed and retained in said reaction element for a time period sufficient for a competitive reaction to occur in the reaction element; and having further provided in fluid communication with said reaction element, (B) a detection element comprising a detection layer which receives a labeled specific component unbound to said protein as a result of said competitive reaction or an optically detectable signal formed dependent on the amount of said labeled specific component.

2. The multilayer analysis element as claimed in claim 1 wherein said reaction element functions to optically block components interfering with optical measurement.

3. The multilayer analysis element as claimed in claim 1 wherein said protein capable of specifically binding to said specific component is not chemically bound to said fibrous porous medium layer.

4. The multilayer analysis element as claimed in claim 1 wherein a reagent layer comprising a porous medium having incorporated therein a labelled complex is further provided on the side opposite said detection layer to said reaction element.

5. The multilayer analysis element as claimed in claim 1 wherein the fibrous porous medium is capable of absorbing at least 50 to 200 μl of a sample solution for competitive immunological reaction.

6. The multilayer analysis element as claimed in claim 1 wherein said reaction element has an area smaller than that of said detection element and which is laminated on said detection element so as not to project from said detection element.

7. The multilayer analysis element as claimed in claim 1 or 2 wherein said specific component and said protein capable of specifically binding thereto is a protein capable of specifically binding so as to form a pair caused by an immunological reaction.

8. The multilayer analysis element as claimed in claim 1 wherein said fine particles are independently separated.

9. The multilayer analysis element as claimed in claim 8 wherein said reaction element has a predetermined area and is prepared by freeze drying a fibrous porous medium containing a predetermined amount of a protein capable of specifically binding to said specific component.

10. the multilayer analysis element as claimed in claim 1 wherein a light shielding layer for optically blocking components interfering with optical measurement is provided between said detection layer and said reaction element.

11. The multilayer analysis element as claimed in claim 10 wherein said light shielding layer is a light reflection layer.

12. The multilayer analysis element as claimed in claim 10 wherein said light shielding layer is a light absorption layer for excitation wavelength and/or fluorescent emission.

* * * * *